United States Patent
Levine et al.

Patent Number: 5,393,674
Date of Patent: Feb. 28, 1995

[54] CONSTITUTENT LAYER HARVESTING FROM A CENTRIFUGED SAMPLE IN A TUBE

[76] Inventors: Robert A. Levine, 31 Pilgrim La., Guilford, Conn. 06437; Stephen C. Wardlaw, 191 N. Cove Rd., Old Saybrook, Conn. 06475

[21] Appl. No.: 25,343

[22] Filed: Mar. 8, 1993

Related U.S. Application Data

[63] Continuation-in-part of Ser. No. 636,260, Dec. 31, 1990, abandoned.

[51] Int. Cl.⁶ .............................................. G01N 1/18
[52] U.S. Cl. .................................... 436/177; 210/787; 210/789; 422/72; 422/101; 422/102; 436/63; 436/180
[58] Field of Search ......................... 436/63, 177, 180; 422/72, 101, 102, 99; 210/789, 787, 242.1, 512.1; 494/16, 20

[56] References Cited

U.S. PATENT DOCUMENTS

| | | | |
|---|---|---|---|
| 3,779,383 | 12/1973 | Ayers | 210/789 |
| 3,814,248 | 6/1974 | Lawhead | 210/789 |
| 3,852,194 | 12/1974 | Fine, Jr. | 210/789 |
| 3,862,042 | 12/1975 | Ayers | 210/789 |
| 3,882,021 | 6/1975 | Ayres | 210/789 |
| 3,891,553 | 6/1975 | Ayres | 210/789 |
| 3,894,950 | 7/1975 | Ayres et al. | 210/789 |
| 3,894,951 | 7/1975 | Ayres | 210/789 |
| 3,897,337 | 7/1975 | Ayres | 210/789 |
| 3,897,343 | 7/1975 | Ayres | 210/789 |
| 4,027,660 | 6/1977 | Wardlaw et al. | 128/771 |
| 4,082,085 | 4/1978 | Wardlaw et al. | 436/63 |
| 4,091,659 | 5/1978 | Massey III et al. | 210/789 |
| 4,159,896 | 7/1979 | Levine et al. | 210/789 |
| 4,853,137 | 8/1989 | Ersson | 422/101 |
| 4,861,477 | 8/1989 | Kimura | 422/72 |
| 4,867,887 | 9/1989 | Smith | 422/101 |
| 4,946,660 | 8/1990 | Fiehler | 436/177 |
| 5,086,784 | 2/1992 | Levine et al. | 210/789 |
| 5,251,474 | 10/1995 | Levine et al. | 210/789 |

*Primary Examiner*—James C. Housel
*Assistant Examiner*—Jan M. Ludlow
*Attorney, Agent, or Firm*—William W. Jones

[57] ABSTRACT

Constituent layers are harvested from a centrifuged multi-constituent material in an evacuated glass or clear plastic tube which contains a float. When possibly contaminated materials, such as blood, are being tested, the use of an evacuated tube allows the measurements to be made without the technician being exposed to the blood. The tubes are large enough to hold approximately one ml of blood, and are filled with an inert gas at low pressure. The floats are formed with a through bore into which cell bands to be harvested will settle during centrifugation. The cell bands are stabilized by a layer of a flowable material which settles onto the plasma layer during centrifugation and forms a pellicle thereon. The cell layers to be harvested are aspirated from the float bore by way of a hypodermic needle or cannula inserted into the tube and float bore.

4 Claims, 2 Drawing Sheets

U.S. Patent  Feb. 28, 1995  Sheet 1 of 2  5,393,674
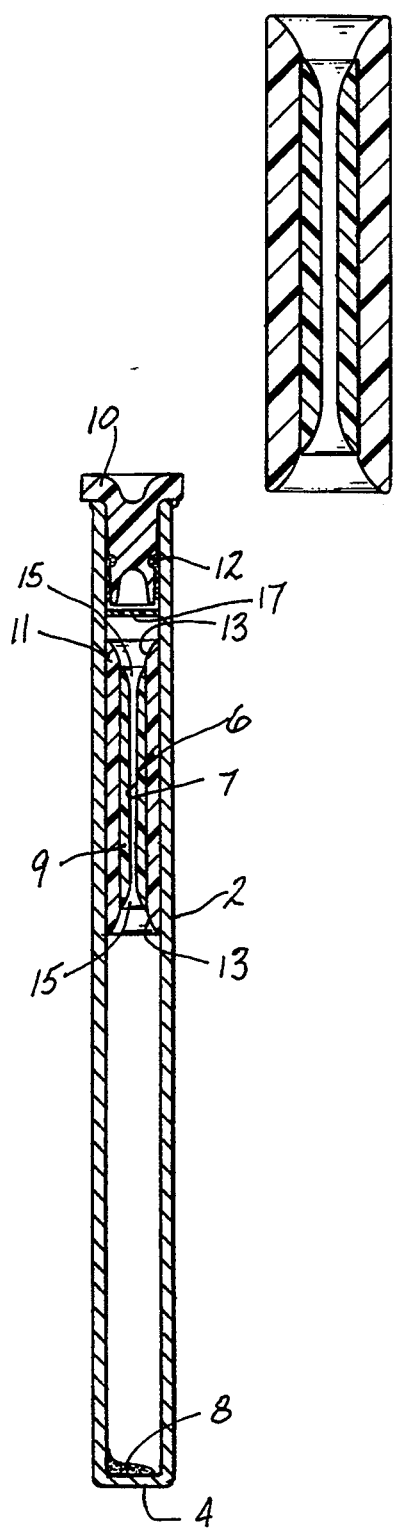
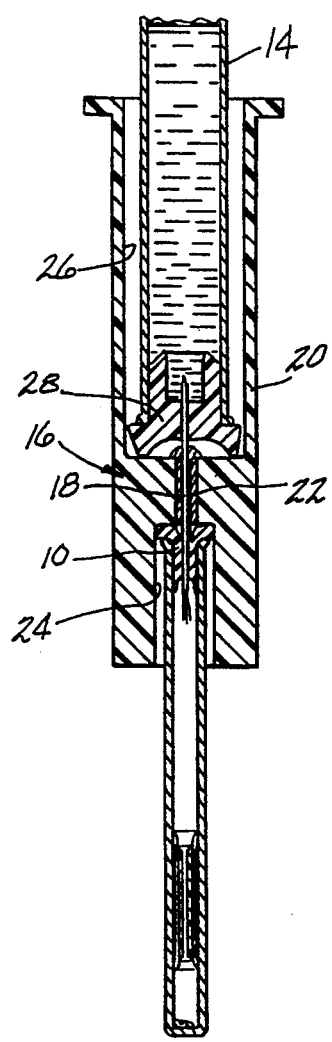
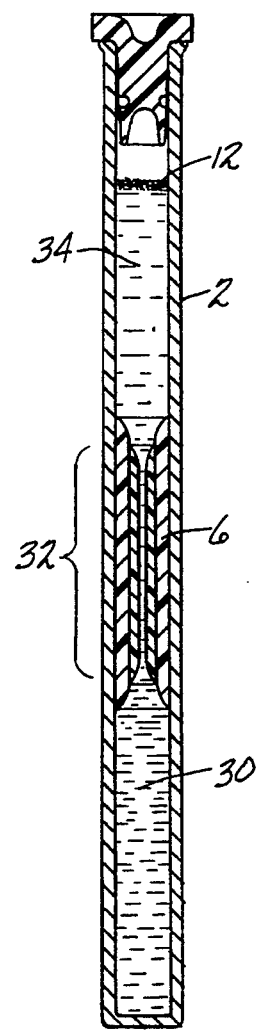
FIG-1   FIG-2   FIG-3   FIG-4

CONSTITUTENT LAYER HARVESTING FROM A CENTRIFUGED SAMPLE IN A TUBE

This is a continuation-in-part of application Ser. No. 07/636,260, filed Dec. 31, 1990, now abandoned.

This invention relates to paraphenalia and a method for determining information about a constituent layer in a centrifuged sample of a material such as anticoagulated whole blood. The constituent layer is harvested from an evacuated tube containing a float which expands the constituent layers being harvested, and which contains a through bore or passage into which the particular constituent layers settle during centrifugation.

A technique has been developed to measure constituent layers in a complex material mixture by centrifuging a sample of the material mixture in a capillary or other tube which contains a float. The float is preferably cylindrical and of a specific gravity which causes it to settle into the centrifuged mixture to a degree which creates a free volume annulus in the tube into which the layer, or layers to be measured will settle. The layers to be measured are thus physically elongated, and can be more easily and accurately measured. This technique is described in U.S. Pat. Nos. 4,027,660, issued Jun. 7, 1977; 4,082,085 issued Apr. 4, 1978; 4,156,570 issued May 29, 1979; and others.

When the material being tested is a possibly contaminated material such as blood, it is desirable to make provisions for protecting the technician against exposure to the blood. When the aforesaid prior art techniques are performed with capillary tubes, the person performing the test is exposed to the blood since the capillary tubes are open-ended. Thus, despite taking normal precautions in handling of the samples, the chance of being contaminated by a blood sample exists. The aforesaid prior art also does not readily lend itself to harvesting of any of the centrifuged blood cell bands from the tube.

This invention is directed to a method and paraphenalia for use in the collecting constituent cells or other particles from a possibly contaminated material such as anticoagulated whole blood, wherein the person doing the collecting is never exposed to the blood. Thus, the possibility of becoming infected by a contaminated blood sample is eliminated. When the tube and float of this invention are used, the blood sample is collected in a sealed tube; then concentration of cells to be harvested is made in the tube; and the cells can be aspirated from the tube without ever exposing the technician to the blood sample. An additional advantage of the invention resides in the fact that it entails the use of a unitary sealed tube which contains all of the required components for use in performing the cell concentration and harvesting, and those components are disposed in a stable, inert environment. The tube used in this invention is preferably a glass tube with an integral closed end. It will be the same length as a capillary tube but will have a larger diameter so as to be able to contain about 0.9 ml of blood. A cylindrical float is disposed inside of the tube, which float has an accurately controlled outside diameter so as to fit snugly in the tube bore under static conditions. When used in harvesting blood cells the float is formed with an axial through bore which receives and expands the white cell and platelet layers in the blood sample after centrifugation thereof. The float is made from a plastic material having a specific gravity that causes it to float in the packed red cells after centrifugation of the blood sample in the tube. Required reagents, such as a stain and a red cell densifier, preferably potassium oxalate, may be disposed in the tube, preferably in liquid form. An elastomeric stopper closes the open end of the tube, and the interior of the tube is filled with an inert gas at low pressure. The low pressure in the tube is used to draw the blood sample into the tube, preferably from a primary blood collection device, such as that sold by Becton Dickinson and Company under the trademark "Vacutainer".

The float may preferably be a compound structure made from plastics which have a specific gravity which causes the float to be buoyed up in the centrifuged red cell layer. The float is formed with a core portion which has the through bore, and an annular sleeve portion which will expand and contract responsive to the magnitude of dynamic forces imposed on the float during performance of the sample centrifugation. The float core must be formed from a plastic material, such as a transparent styrene, which is dimensionally stable during centrifugation. The peripheral sleeve portion of the float can be formed from a transparent pliable vinyl plastic. The two components of the float can be joined together by co-extruding or by co-molding the float components. The tube can be provided with a lubricant coating, such as a silicone coating to enhance movement of the float in the tube during centrifugation. Specific plastics which can be used for the core and sleeve of the float are polystyrene and polyvinylchloride (PVC) respectively. The float may also be formed from a single plastic material if so desired.

The primary blood collection tube which will preferably contain the anticoagulant will be provided with a needle which is used to pierce the elastomeric stopper in the tube of this invention, whereupon the blood will flow from the collection tube, through the needle, into the testing tube. In order to preserve cell band formation in the tube when the tube and blood are centrifuged, a thixotropic gel would be disposed in the top of the tube. During centrifugation, the gel will flow down the wall of the tube and settle on top of the plasma layer to form a viscous pellicle on the plasma. Obviously, the gel must have a specific gravity which is less than that of the plasma. A thin plastic cup may be used in lieu of the gel.

When the larger bore diameter tube and the larger float with an axial bore are used per this invention, there occurs a relaxation in the diameter dimensional tolerances in the tube bore ID. It is desirable to achieve a ten fold expansion of the white cell and platelet layers when performing the cell harvesting with the tube-float combination of the aforesaid prior art. When using the enlarged tubes and floats of this invention, the ten fold expansion can be obtained from a through bore diameter of 1.265 mm when a 4.0 mm diameter tube bore is used. This compares with a free space of about 43 microns with the prior art capillary tubes and floats. The +/− variation in the bore diameter is 20 microns when using the paraphenalia of this invention.

A benefit deriving from the use of the larger tube and float paraphenalia is an improvement in the hydrodynamics of the centrifugation. After blood is added to the tube, the tube is centrifuged at 10,000 G, as is the usual practice. With a float of this type, several forces are brought into play. First, the centripedal accelleration forces the float to the end of the tube at the same time as the blood cells are separating. Secondly, a tidal force is exerted on the float because the accelleration is unequal at the ends of the float. This tidal force is about 2,000 G at near the center of the tube. This exerts a stretching or contracting force on the float of about 500 G, which is enough to sufficiently elongate the pliable elastomeric portion of the float and slightly decrease its diameter, allowing it to easily slip down the tube. After the float settles according to its density into the RBC layer, and the centrifuge slows to a stop, the tidal forces cease, and the float relaxes to its normal diameter thereby reassuming its close approximation to the walls of the tube.

The cells and components of the buffy coat layer are expanded linearly in the narrow bore channel in the float and thus can be easily harvested therefrom.

It is therefore an object of this invention to provide an improved blood sampling paraphenalia which allows for the blood cell harvesting to be made without exposing the technician to contamination from the blood sample.

It is a further object of this invention to provide blood sampling paraphenalia of the character described wherein dimensional tolerances are relaxed while providing the necessary cell layer expansion.

It is an additional object of this invention to provide blood sampling paraphenalia of the character described wherein larger blood samples are used.

It is still another object of this invention to provide blood sampling paraphenalia of the character described wherein the formation of cell bands after centrifugation, is stabilized and preserved.

It is yet an additional object of this invention to provide blood sampling paraphenalia of the character described wherein improved hydrodynamics during centrifugation is achieved.

These and other objects and advantages of the invention will become more readily apparent from the following description of a preferred embodiment thereof when considered in conjunction with the accompanying drawings, in which:

FIG. 1 is an axial sectional view of a preferred embodiment of a tube and float assembly formed in accordance with this invention.

FIG. 2 is an axial sectional view of the float;

FIG. 3 is an axial sectional view showing how the assembly can be used to draw a blood sample from a primary blood collecting tube;

FIG. 4 is a view similiar to FIGS. 1 and 3 but showing the assembly of FIG. 1 after the blood sample has been drawn and centrifuged.

Figure 5:
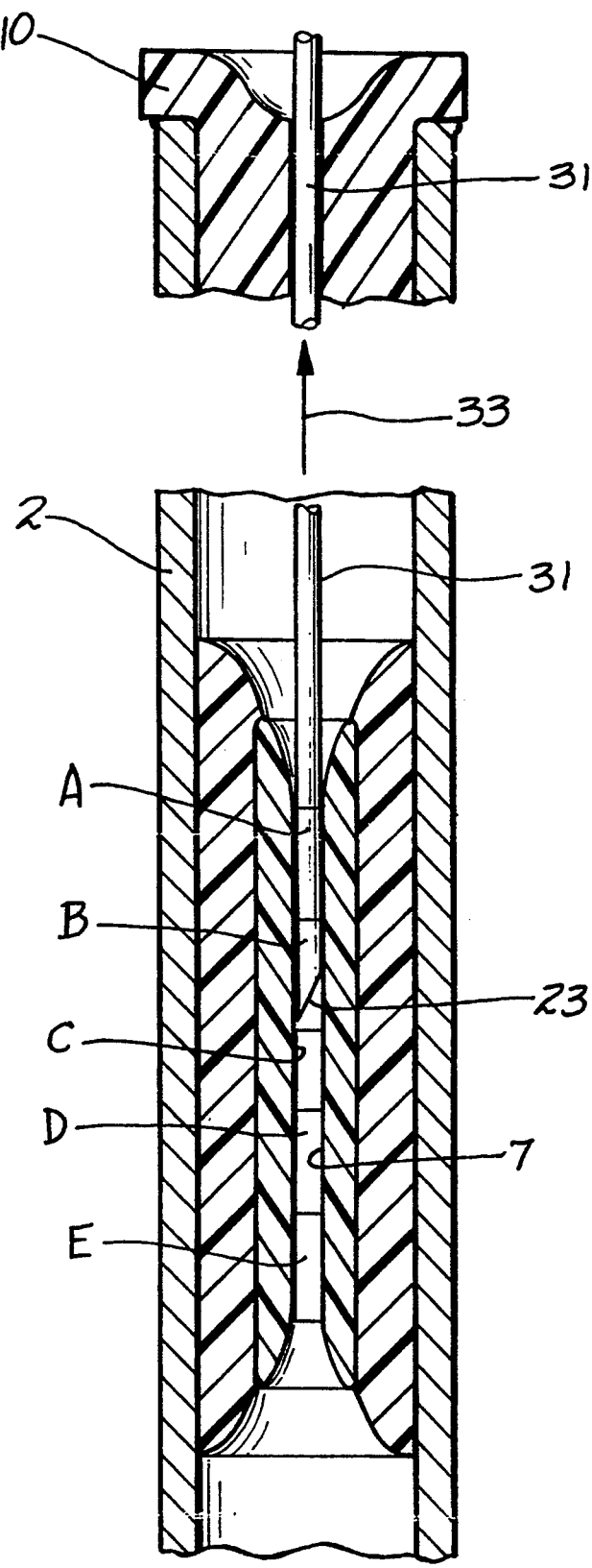
FIG. 5 is a fragmented sectional view showing how a cell layer can be harvested from the centrifuged sample.

Referring now to the drawings, there is shown in FIG. 1 a preferred embodiment of the blood sampling paraphenalia formed in accordance with this invention. The blood sampling paraphenalia includes a transparent tube 2 formed preferably of glass, and having an integrally closed end 4. A plastic float member 6 is disposed in the tube 2, as are the stain and red cell densifier reagents 8. An elastomeric plug 10 closes the open end of the tube 2, and a supply of a thixotropic gel 12 is disposed inside of the tube 2 around the plug 10. In place of the gel 12, a thin plastic disc or cup 17 can be used. The tube is preferably about 75 mm long, the same length as a capillary tube, and has a bore diameter of about 40 mm. Its capacity for blood is about 0.9 ml. The float will be about 8 mm in length and about 4 mm in diameter when static in the tube.

The float 6 is a compund structure which has a central through bore 7 into which the white cells and platelets layer out during centrifugation. The bore 7 is preferably about 1.265 mm in diameter so as to achieve the necessary cell band elongation to allow harvesting of the target cell band. The float 6 is formed with a core part 9 made from a dimensionally stable transparent plastic, such as a rigid styrene plastic. A sleeve part 11 surrounds the core 9 and is bonded thereto. The sleeve 11 is formed from a pliable transparent plastic such as PVC. The ends of the sleeve 11 are flared, as at 13, and the ends of the bore 7 are also flared as at 15 to allow movement of the blood in the tube 2 during filling and centrifugation.

FIG. 3 shows how the tube 2 can be filled with blood from a primary blood collecting tube 14 by means of a transferring device 16 having a double piercing needle or cannula 18. The transfer device 16 includes an outer shroud 20 with a needle-carrying plug 22 telescoped thereinto. The needle 18 extends into a first well 24 in the plug 22 sized to receive the stoppered end of the blood sampling tube 2. The shroud 20 forms a second well 26 which is sized to receive the stoppered end of the primary blood collecting tube 14. The transfer needle 18 pierces the plug 28 in the tube 14 and also pierces the plug 10 in the sampling tube 2. The low pressure in the tube 2 causes blood to be drawn from the tube 14 through the needle 18 into the tube 2, the flow of blood continuing until the tube 2 is substantially filled. Once filled, the tube 2 is withdrawn from the well 24 and centrifuged. While transferring blood to the testing tube 2 from a collection tube 14 is one way to fill the tube 2, it is readily apparent that the sample could be taken directly from a patient using a needle and the evacuated tube 2.

When the blood enters the tube 2, the reagents 8 will mix with the blood, and the tube 2 will be ready to centrifuge. The tubes 2 are oriented in the centrifuge with the closed end 4 out, so that the red cells will settle in the closed end of the tube 2 and the plasma will be adjacent to the stoppered end of the tube 2 after centrifugation. FIG. 4 shows the condition of the tube 2 and blood after the centrifugation has been completed. The red cells 30 collect in the closed end of the tube 2 and the float 6 becomes embedded in, and projects above the top of the red cell layer. The white cells and platelet layers which make up the buffy coat 32 settle into the axial through bore 7 in the float 10 and the plasma 34 is disposed above the buffy coat and float 10. The thixotropic gel 12 (or plastic disc 17) covers and floats on the plasma layer 34 thereby holding the centrifuged blood constituent layers in place in the bore 7 when the tube 2 is handled after the centrifugation step during harvesting of the target cell band from the float bore 7.

FIG. 5 shows the manner in which the target cells can be harvested from the float bore 7 with an aspirating needle 31. The needle 31 is inserted into the tube 2 through the plug 10 so that its tip 23 may be positioned in the target cell band B, the other cell bands being designated A, C, D and E. Suction is applied to the band B via the needle 31 causing the cells to move in the direction of the arrow 33 into the needle 31.

When the filled tube 2 is subjected to centrifugation forces of 10,000 G, which is the force at which the prior art capillary tubes are centrifuged, the pliable sleeve part 11 of the float 6 radially contracts whereby the effective diameter of the float 6 decreases. Thus the float 6 is forced through the blood sample until the float encounters the centrifuged red cell layer which, because of its specific gravity, resists further movement of the float 6. Once this occurs, the float 6 will be stabilized and the sleeve part 11 will expand back outwardly into snug engagement with the tube bore. The tube bore wall may be coated with a silicone lubricant to enhance the slidability of the float 6 in the tube 2.

It will be readily appreciated that the tubes of this invention can be used to draw blood samples from patients or from blood collecting tubes, and the blood cell measurements can then be made directly in the stoppered, closed tubes without exposing anyone to the possibility of contact with contaminated blood. Thus the blood testing procedure can even be used with patients who are known to have contaminated blood with no danger to the person doing the testing. The dimensional tolerances observed in producing the tubes and floats are relaxed, and the test assemblies have a longer shelf life since the interior of the evacuated tubes is filled with an inert gas. Cell layer band formation is preserved during handling of the tube after centrifugation due to the pellicle formed on top of the plasma by the thixotropic material or by a plastic disc in the tube during centrifugation. Target cells can be easily harvested from the readily visible, elongated bands of cells in the float bore.

Since many changes and variations of the disclosed embodiment of the invention may be made without departing from the inventive concept, it is not intended to limit the invention otherwise than as required by the appended claims.

What is claimed is:

1. A method for harvesting target cells from a centrifuged sample of anticoagulated whole blood contained in a tube which also contains a cylindrical float having a through passage for receiving and elongating layers of blood cell components to be harvested from the sample, the float having an axially constant outer diameter which ensures that the float fits snugly in the tube when under static conditions, said method comprising the steps of:
   a) drawing a blood sample into the tube;
   b) centrifuging the blood, tube and float at sufficient G forces to move the float toward one end of the tube, and concurrently exerting a tidal force on the float during centrifugation to contract the outer diameter of the float sufficiently to allow the float to slide through the tube during the centrifugation step;
   c) forcing said blood cell components to settle in said through passage; and
   d) removing said blood cells from said through passage and said tube by means of an aspirating cannula inserted into said through passage.

2. The method of claim 1 further comprising the step of lubricating the interface between the tube and float to enhance movement of the float through the tube.

3. The method of claim 2 further comprising the step of evacuating said tube to an extent needed to automatically draw blood into said tube.

4. A method for harvesting a target constituent from a centrifuged sample of anticoagulated whole blood sample contained in a tube which tube also contains a float having a through passage for receiving and elongating all of the target constituent, the float having an outer diameter which ensures that the float fits snugly in the tube when under static conditions, said method comprising the steps of:
   a) drawing the material sample into the tube;
   b) centrifuging the material sample, the tube and the float at adequate G forces to move the float toward one end of the tube sufficiently that the target constituent settles into the through passage in the float and is thereby physically elongated; and
   c) inserting a cannula into said through passage and aspirating the target constituent out of the float through passage through said cannula without removing any of the rest of the material sample from the tube.

* * * * *